United States Patent
Rey et al.

(10) Patent No.: US 11,220,474 B2
(45) Date of Patent: Jan. 11, 2022

(54) METHOD FOR SYNTHESISING VITAMIN A

(71) Applicant: ADISSEO FRANCE S.A.S., Antony (FR)

(72) Inventors: Patrick Rey, Lyons (FR); Robert Huet, Paris (FR); Sylvain Aubry, Calais (FR); Vivien Henryon, Lyons (FR)

(73) Assignee: ADISSEO FRANCE S.A.S., Antony (FR)

( * ) Notice: Subject to any disclaimer, the term of this patent is extended or adjusted under 35 U.S.C. 154(b) by 0 days.

(21) Appl. No.: 17/269,095

(22) PCT Filed: Aug. 19, 2019

(86) PCT No.: PCT/EP2019/072083
§ 371 (c)(1),
(2) Date: Feb. 17, 2021

(87) PCT Pub. No.: WO2020/038857
PCT Pub. Date: Feb. 27, 2020

(65) Prior Publication Data
US 2021/0309596 A1   Oct. 7, 2021

(30) Foreign Application Priority Data
Aug. 20, 2018   (FR) ...................................... 1857548

(51) Int. Cl.
*C07C 45/67* (2006.01)
*C07C 29/14* (2006.01)
*C07C 45/65* (2006.01)

(52) U.S. Cl.
CPC .............. *C07C 45/65* (2013.01); *C07C 29/14* (2013.01); *C07C 2601/16* (2017.05)

(58) Field of Classification Search
CPC .......... C07C 45/65; C07C 45/67; C07C 29/14
See application file for complete search history.

(56) References Cited

PUBLICATIONS

Alain Valla et al. "New Syntheses of Retinal and Its Acyclic Analog y-Retinal by an Extended Aldol Reaction with a C6 Building Block That Incorporates a C5 Unit after Decarboxylation. A Formal Route to Lycopene and B-Carotene", Helvetica Chimica Acta, 2007, vol. 901, pp. 512-520.
International Search Report dated Nov. 12, 2019 re: Application No. PCT/EP2019/072083, pp. 1, citing: Alain Valla et al. "New Syntheses of Retinal . . . . "
International Report on Patentability dated Feb. 23, 2021 re: Application No. PCT/EP2019/072083, pp. 1-5, citing: Alain Valla et al. "New Syntheses of Retinal . . . . "

*Primary Examiner* — Sikarl A Witherspoon
(74) *Attorney, Agent, or Firm* — Cantor Colburn LLP

(57) ABSTRACT

A method for preparing dehydro-cyclofarnesal from dehydro-farnesal by cyclization in the presence of an acid may include the dehydro-farnesal being obtained from the farnesal by dehydrogenation and may further includes the cyclization being carried out in the presence of an acid selected from Lewis acids, Bronstedt acids, and zeolites. The synthesis of vitamin A using this method further includes the conversion of dehydro-cyclofarnesal into vitamin A.

10 Claims, No Drawings

METHOD FOR SYNTHESISING VITAMIN A

TECHNICAL FIELD

The present disclosure concerns new reactions for transforming sesquiterpene compounds making it possible to open a pathway of access to vitamin A ($C_{20}H_{30}O$), its precursors and its derivatives.

BACKGROUND

The industrial-scale synthesis of vitamin A is carried out by various conventional methods. Among other preparations, vitamin A can be obtained by the so-called C15+C5 condensation pathway, for example the so-called Julia reaction which involves the chemistry of sulfones, according to which the vinyl-β-ionol is treated with a phenylsulfinate anion for leading to a C15 sulfone to which an allyl bromide is added to obtain a C20 sulfone. This is then converted, by elimination, into vitamin A acetate which is generally used as is, the vitamin A being very unstable, or saponified into vitamin A.

Other methods are also used. Thus, the vitamin A can be made by a C15+C5 coupling method via a Wittig reaction; this method nonetheless implements intermediates with carcinogenic, mutagenic or toxic effects for the reproduction (CMR), such as C5 acetate, and requires a unit for regenerating phosphine with phosgene, which is a very toxic gas.

Another pathway of access lies in a C6+C14 coupling method through alkyne chemistry; it has the drawbacks of using certain raw materials, such as acetylene and nButyl-Li, which present obvious HSE (Health-Safety-Environment) risks and of involving epoxy intermediates that are not very stable and toxic.

In the document A Valla et al., Helvetica Chimica Acta, vol. 90 (2007) 512-520 concerning the preparation of retinal, the aldehyde form of vitamin A, the authors describe the two-step synthesis of dehydro-cyclofarnesal from β-ionone. This synthesis passes through a C15 nitrile intermediate which is reduced by diisobutylaluminum hydride into dehydro-cyclofarnesal.

SUMMARY

However, these synthetic methods have not undergone any real changes since their discovery, and to date, it is important to use new industrial synthesis methods that are safer and more economical.

The disclosure provides a new pathway for the synthesis of vitamin A, from sesquiterpenes, and in particular farnesene, farnesal and farnesol, or sesquiterpene derivatives, and in particular nerolidol and dehydronerolidol. These compounds are present in nature, they are found in certain plant essences and in or on the surface of certain fruits, from which they can be extracted, they are also biosynthesized by microorganisms, in particular fungi. As the reagent resource is therefore inexhaustible, the disclosure provides a lasting solution to the cost problems of conventional methods and contributes to real progress in the manufacture of vitamin A, but also that of intermediates for other syntheses.

Among the reactions which are the subject of the present disclosure, one constitutes a key step in the synthesis of vitamin A. This is a method for preparing dehydro-cyclofarnesal from dehydro-farnesal by cyclization in the presence of an acid.

The reaction for converting dehydro-farnesal into dehydro-cyclofarnesal according to the disclosure constitutes an important step in the chain of synthesis of vitamin A, its precursors or its derivatives, in that it allows access to a C15 structure containing the vitamin A cycle without resorting to vinyl-β-ionol.

The dehydro-farnesal can be obtained by dehydrogenation of farnesal according to a reaction which is also an advantage of the disclosure, which is advantageous because farnesal is an easily accessible reagent. It can in fact be produced synthetically from farnesene, farnesol, ethyl farnesoate, nerolidol or dehydro-nerolidol according to methods known to one skilled in the art ((Tetrahedron Letters 2016, 57, 40, 4496-4499; New Journal of Chemistry 2001, 25, 7, 917-929; Catal. Comm. 2014, 44, 40-45), but it is also being isolated from essential oils, such as those of lemongrass.

As indicated above, farnesal can be made from farnesene, and in particular it can be prepared by oxidation of farnesene according to a method which is yet another advantage of the disclosure.

Before discussing the disclosure in more detail, the definitions of terms used in this text are given below.

All reference to an unsaturated compound extends to the isomers of that compound, in particular to its regioisomers and stereoisomers.

By way of example, the term farnesene includes the alpha and beta regioisomers of farnesene, as well as the stereoisomers of each of them, as illustrated below:

α-farnesene (3,7,11-trimethyl-1,3,6,10-dodecatetraene) having the following formula

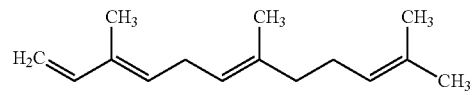

which can exist as the following 4 isomers (3E, 6E), (3E, 6Z), (3Z, 6Z) and (3Z, 6E), and β-farnesene (7,11-dimethyl-3-methylene-1,6,10-dodecatriene) having the following formula

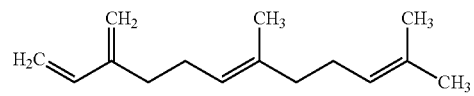

which can exist in the form of the following 2 isomers (6E) and (6Z).

By way of another example, the term cyclofarnesal covers the following two regioisomers:

cyclofarnesal of formula:

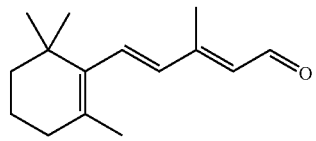 [SMILES: CC1=C(/C=C/C(C)=C/C=O)C(C)(C)CCC1]

and its isomers E, Z cyclofarnesal enol of formula:

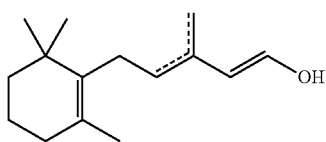

and its isomers E, Z.

This definition applies in particular to farnesal, dehydro-farnesal, dehydro-cyclofarnesal, farnesol, nerolidol, dehydro-nerolidol, retinal, whose names cover all their respective isomers.

The term acid means any inorganic or organic compound, in any form, in particular liquid, solid or gas, present in the reaction medium in a homogeneous or heterogeneous phase, and having an electronic gap making it capable of accepting a pair of electrons.

The disclosure is exposed in more detail below.

DETAILED DESCRIPTION OF THE DISCLOSURE

The disclosure thus concerns the cyclization of dehydro-farnesal to dehydro-cyclofarnesal carried out in the presence of an acid. Advantageously, the acid is selected from Lewis acids, Bronstedt acids and zeolites, and any combination thereof. By way of example, it can be chlorosulfonic acid, boron trifluoride or an etherate thereof, or even tin chloride.

The disclosure also concerns the manufacture of dehydro-farnesal from farnesal by catalytic dehydrogenation. Under preferred conditions, this dehydrogenation is carried out in the presence of one or more palladium (II) salts. Use will advantageously be made of salts of Pd(OAc)$_2$ type, a base and an oxidizing agent.

Typically, the conditions for this reaction are as follows: Pd(OAc)$_2$, a base selected from Na$_2$CO$_3$ and K$_2$CO$_3$, and in the presence of oxygen. The use of protic polar type solvents is more particularly indicated with, for example, the use of dimethylsulfoxide (DMSO), N-methylpyrrolidone (NMP) or dimethylol-ethylene urea (DMEU). These conditions can be supplemented by the presence of ligands selected in particular from aromatic compounds such as hydroquinone, catechol or diazafluorenone, or precursor additives of pi-allyl such as allyl diethylphosphate.

The disclosure also provides a method for oxidizing farnesene into farnesal. This reaction is carried out under the catalytic conditions of a Wacker-type method in the presence of at least one precious metal, mainly palladium. Advantageously, the reaction medium comprises palladium (II) salts such as PdCl$_2$, copper salts and an oxidizing agent. For example, the reaction is carried out in the presence of PdCl$_2$(CH2CH2), CuCl$_2$—LiMoO$_4$.

The disclosure also concerns the manufacture of dehydro-farnesal from farnesene, according to a method implementing the aforementioned steps, namely: oxidation of farnesene to farnesal, then dehydrogenation of farnesal to dehydro-farnesal, these two steps being carried out under the conditions of the disclosure described above.

Another of the advantages of the disclosure is a method for synthesising vitamin A from farnesene, which comprises at least one of the steps described above, namely:
cyclization of dehydro-farnesal into dehydro-farnesal;
oxidation of farnesene into farnesal;
dehydrogenation of farnesal into dehydro-farnesal.

Advantageously, the method for synthesising vitamin A comprises at least two, or even all of these steps, and is followed by a conversion of dehydro-cyclofarnesal into vitamin A, according to a method within the reach of one skilled in the art having an average level of knowledge. According to an advantageous variant of the disclosure, vitamin A is obtained by reacting dehydro-cyclofarnesal with a silyl enol ether of prenal, for example a trimethylsilyl enol ether, resulting in retinal.

The disclosure is hereinafter illustrated in examples carried out under reaction conditions which support the practice of the disclosure but to which it is certainly not restricted.

In the examples, the used abbreviations are defined below:
TT defines the conversion rate;
RR defines a yield on reagent;
Assayed RR defines a yield on reagent assayed in a reaction medium.

Example 1: Cyclization of Dehydro-Farnesal into Dehydro-β-Cyclofarnesal

The cyclization of dehydro-farnesal to dehydro-β-cyclofarnesal is carried out according to the scheme hereinbelow:

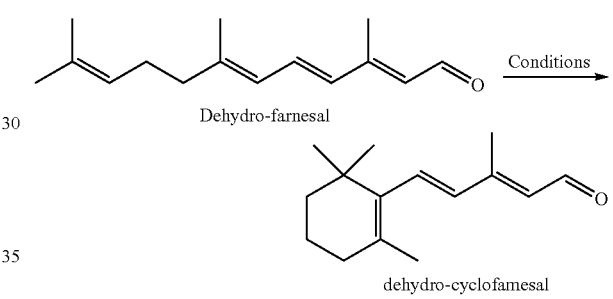

The operating conditions are as follows:

Dehydro-farnesal (0.115 mmol), the solvent (0.46 mL) and finally the source of acid, added at the indicated temperature, are introduced into a 4 mL vial fitted with a magnetic bar and placed under a nitrogen atmosphere. The reaction medium is then stirred with magnetic stirring at the specified temperature. The times indicated in the table correspond to the best obtained yields. The samples (200 µL) are analyzed by gas chromatography (GC). Different conditions were tested, the most representative are indicated in Table 1.

TABLE 1

| Conditions | $TT_{dehydrofarnesal}$ (GC, %) | assayed $RR_{dehydro-β-cyclofarnesal}$ (GC, %) |
|---|---|---|
| ClSO$_3$H, CH$_2$Cl$_2$, −78° C., 30 min. | 94 | 22 |
| SnCl$_4$ (2 éq.), toluene, 0° C., 30 min. | 100 | 35 |
| BF$_3$ · Et$_2$O (2 eq.), toluene, 30° C. | 100 | 14 |

Example 2: Oxidation of β-Farnesene into Farnesal

The oxidation of β-farnesene in farnesal is carried out according to the scheme below:

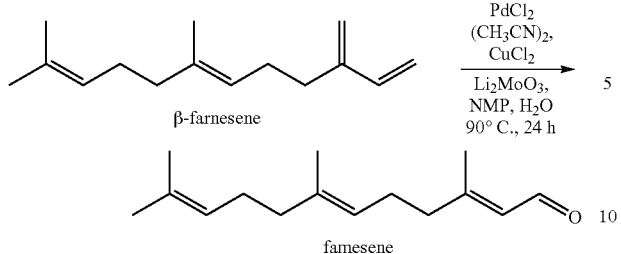

The operating conditions are as follows:

PdCl$_2$(CH$_3$CN)$_2$ (0.25 mmol), Li$_2$MoO$_4$ (1.7 mmol), CUCl$_2$ (0.3 mmol), the solvent (2 mL), H$_2$O (0.2 mL) and alkene (1.0 mmol) are introduced into a 4 mL vial fitted with a magnetic bar, and placed under a nitrogen atmosphere. The reaction medium is then stirred with magnetic stirring at 90° C. The times indicated in the table below correspond to the best obtained yields. The samples (200 μL) are analyzed by GC.

TABLE 2

| Conditions | Solvent | TT$_{farnesene}$ (GC, %) | Assayed RR$_{farnesal}$ (GC, %) |
|---|---|---|---|
| β-farnesene, 24 h, 90° C. | NMP | 73 | 17 |
|  | DMEU | 75 | 13 |
|  | DMSO | 57 | 6 |

Example 3: Dehydrogenation of Farnesal into Dehydro-Farnesal

The dehydrogenation of the farnesal into dehydro-farnesal is carried out according to the scheme below:

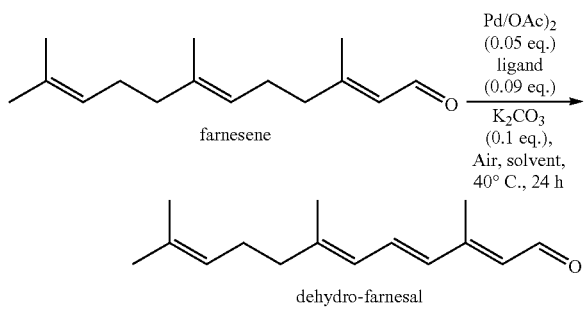

The operating conditions are as follows:

Pd(OAc)$_2$ (0.03 mmol), K$_2$CO$_3$ (0.05 mmol), 4,5-diazafluorenone (DAF) (0.045 mmol), the solvent (0.46 mL) and the farnesal (0.5 mmol) are introduced into an open 4 mL vial fitted with a magnetic bar, and placed under a nitrogen atmosphere. The reaction medium is then stirred with magnetic stirring at 30° C. The samples (approximately 200 μL) are taken after 1 h, 3 h, 5 h, 7 h, 24 h and then analyzed by GC.

These conditions lead to a TT$_{farnesal}$ (GC,%) of 92% and an assayed RR$_{dehydrofarnesal}$ (GC,%) of 60%.

Example 4: Preparation of Retinal from Dehydro-Cyclofarnesal

The retinal is prepared according to the scheme below:

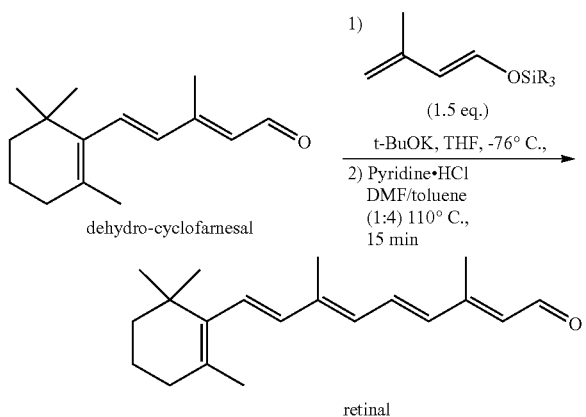

In detail, this transformation takes place under the following conditions, passing through non-isolated intermediates:

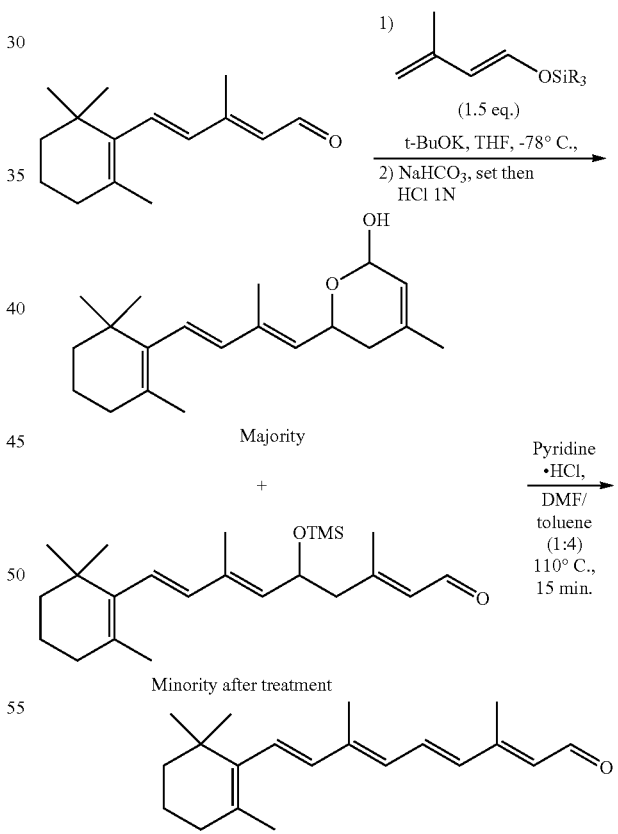

These conditions lead to a TT$_{dehydro-β-cyclofarnesal}$ (TLC) of 100% and an assayed RR$_{retinal}$ of 40%.

The invention claimed is:
1. A method for preparing dehydro-cyclofarnesal from dehydro-farnesal by cyclization in the presence of an acid.

2. The method according to claim 1, wherein the cyclization is carried out in the presence of an acid selected from Lewis acids, Bronstedt acids, and zeolites.

3. The method according to claim 2, wherein the acid is selected from chlorosulfonic acid, boron trifluoride and its etherates, and tin chloride.

4. The method according to claim 1, wherein the dehydro-farnesal is obtained from farnesal by dehydrogenation.

5. The method according to claim 4, wherein the dehydrogenation of the farnesal is carried out in the presence of at least one palladium (II) salt.

6. The method according to claim 4, wherein the farnesal is obtained from farnesene, farnesol, ethyl farnesoate, nerolidol, or dehydro-nerolidol.

7. The method according to claim 4, wherein the dehydro-farnesal is obtained from farnesene, and in that the method further includes the following steps:
   oxidation of farnesene into farnesal, then
   dehydrogenation of farnesal into dehydro-farnesal.

8. The method according to claim 7, wherein the oxidation of farnesene is carried out under catalytic conditions of the Wacker type in the presence of at least one precious metal such as palladium.

9. A method for synthesising vitamin A from farnesene, wherein it comprises at least one method according to claim 7, then the conversion of dehydro-cyclofarnesal into vitamin A.

10. The method for synthesising vitamin A according to claim 9, wherein the dehydro-cyclofarnesal is converted into vitamin A by reaction with a silyl enol ether of prenal.

* * * * *